United States Patent
DeWaard (10) Patent No.: US 9,751,787 B1
(45) Date of Patent: Sep. 5, 2017

(54) ANAEROBIC DIGESTING SYSTEMS AND METHODS FOR PROCESSING ANIMAL WASTE

(75) Inventor: David DeWaard, Lynden, WA (US)

(73) Assignee: Daritech, Inc., Lynden, WA (US)

( * ) Notice: Subject to any disclaimer, the term of this patent is extended or adjusted under 35 U.S.C. 154(b) by 1092 days.

(21) Appl. No.: 13/592,170

(22) Filed: Aug. 22, 2012

Related U.S. Application Data (60) Provisional application No. 61/526,617, filed on Aug. 23, 2011.

(51) Int. Cl.
*C02F 11/04* (2006.01)
*C02F 3/12* (2006.01)

(52) U.S. Cl.
CPC ............... *C02F 3/12* (2013.01); *C02F 11/04* (2013.01)

(58) Field of Classification Search
None
See application file for complete search history.

(56) References Cited

U.S. PATENT DOCUMENTS

| | | |
|---|---|---|
| 1,493,091 A | 5/1924 | Wiggins |
| 1,693,857 A | 12/1928 | Moser |
| 1,716,491 A | 6/1929 | Griffin |
| 2,041,318 A | 5/1936 | Berger |
| 2,056,857 A | 10/1936 | Inboden et al. |
| 2,497,047 A | 2/1950 | Prager et al. |
| 2,497,645 A | 2/1950 | Wiggins |
| RE23,417 E | 10/1951 | Prager et al. |
| 2,722,357 A | 11/1955 | Whitecar |
| 2,789,722 A | 4/1957 | Oberst |
| 2,808,958 A | 10/1957 | Wiggins |
| 2,844,169 A | 7/1958 | Skinner |
| 2,948,593 A | 8/1960 | Larson |
| 3,041,148 A | 6/1962 | Ballantyne et al. |
| 3,074,587 A | 1/1963 | Jennings |
| 3,158,667 A | 11/1964 | Michaels |
| 3,178,267 A | 4/1965 | Larson |
| 3,251,471 A | 5/1966 | Allen |
| 3,535,236 A | 10/1970 | Travis |
| 3,535,712 A | 10/1970 | Zeff et al. |
| 3,676,074 A | 7/1972 | Shibayama et al. |
| 3,679,053 A | 7/1972 | Koulovatos et al. |

(Continued)

FOREIGN PATENT DOCUMENTS

| | | |
|---|---|---|
| CA | 2336838 | 6/2001 |
| CA | 2690420 | 7/2010 |

(Continued)

OTHER PUBLICATIONS

FR2872676A1, Google Machine Translation, 2015, 20 pages.

*Primary Examiner* — Chester Barry
(74) *Attorney, Agent, or Firm* — Michael R. Schacht; Schacht Law Office, Inc.

(57) ABSTRACT

A digester system for digesting feed material comprises a digester tank, a thickener, and a seal system. The digester tank generates a first digested material and biogas from the feed material. The thickener is operatively connected to the digester tank to remove a second digested material from the feed material to alter a solid content of the feed material in the digester tank. The seal system substantially prevents the thickener from removing biogas from the feed material with the second digested material.

39 Claims, 8 Drawing Sheets

(56) References Cited

U.S. PATENT DOCUMENTS

| | | | |
|---|---|---|---|
| 3,874,175 A | 4/1975 | Winters |
| 3,922,514 A | 11/1975 | Greenhut |
| 3,950,249 A | 4/1976 | Eger et al. |
| 3,952,421 A | 4/1976 | Wilson et al. |
| 4,154,685 A | 5/1979 | Marcotte |
| 4,342,383 A | 8/1982 | Burnett |
| 4,419,550 A | 12/1983 | Monette |
| 4,473,467 A | 9/1984 | Marcotte |
| 4,633,535 A | 1/1987 | Louvo |
| 4,836,918 A | 6/1989 | Szikriszt |
| 5,033,863 A | 7/1991 | Linkletter |
| 5,292,637 A | 3/1994 | Bohnensieker |
| 5,300,438 A | 4/1994 | Augspurger et al. |
| 5,357,855 A * | 10/1994 | Ishigaki .................. B30B 9/12 100/112 |
| 5,407,809 A | 4/1995 | Finn |
| 5,409,610 A | 4/1995 | Clark |
| 5,534,437 A | 7/1996 | Arrau |
| 5,586,731 A | 12/1996 | Glaze et al. |
| 5,589,391 A | 12/1996 | Fink |
| 5,593,888 A | 1/1997 | Glaze et al. |
| 5,618,424 A | 4/1997 | Nagaoka |
| 5,661,031 A | 8/1997 | Murphy et al. |
| 5,716,013 A | 2/1998 | Benson et al. |
| 5,759,850 A | 6/1998 | Seymour |
| 5,776,768 A | 7/1998 | Seymour et al. |
| 5,887,908 A | 3/1999 | White |
| 5,922,094 A * | 7/1999 | Richards .................. F16T 1/00 137/177 |
| 5,925,561 A | 7/1999 | Posselius, Jr. et al. |
| 6,056,800 A | 5/2000 | Carter, IV |
| 6,105,536 A | 8/2000 | DeWaard |
| 6,281,001 B1 | 8/2001 | McNelly |
| 6,397,492 B1 | 6/2002 | Malley |
| 6,443,094 B1 | 9/2002 | DeWaard |
| 6,783,975 B2 | 8/2004 | Windle |
| 6,997,135 B1 | 2/2006 | DeWaard |
| 7,056,441 B1 | 6/2006 | Menke et al. |
| 7,138,271 B2 | 11/2006 | Pratte |
| 7,270,754 B2 | 9/2007 | Menke et al. |
| 7,306,731 B1 | 12/2007 | DeWaard |
| 7,468,132 B2 | 12/2008 | Zotter et al. |
| 7,631,595 B1 | 12/2009 | DeWaard |
| 7,708,885 B2 | 5/2010 | Lanting et al. |
| 7,721,903 B2 | 5/2010 | Ben Afeef |
| 7,987,778 B1 | 8/2011 | Dewaard |
| 8,142,667 B2 | 3/2012 | DeWaard |
| 8,201,495 B2 | 6/2012 | DeWaard |
| 2001/0040131 A1 | 11/2001 | Yamane |
| 2002/0006075 A1 | 1/2002 | Ferris et al. |
| 2005/0089998 A1 | 4/2005 | Miller |
| 2006/0154362 A1 | 7/2006 | Sundberg |
| 2008/0093292 A1 | 4/2008 | Zotter et al. |
| 2008/0277336 A1 | 11/2008 | Dvorak |
| 2009/0065448 A1 | 3/2009 | Schedler |
| 2009/0200231 A1 | 8/2009 | Walton et al. |
| 2009/0249685 A1 | 10/2009 | Flowers et al. |
| 2010/0112632 A1 | 5/2010 | DeWaard |
| 2011/0100930 A1 | 5/2011 | DeWaard |
| 2011/0198268 A1 | 8/2011 | DeWaard |
| 2011/0253227 A1 | 10/2011 | DeWaard |
| 2011/0309039 A1 | 12/2011 | DeWaard |
| 2012/0000863 A9 | 1/2012 | DeWaard |
| 2012/0138515 A1 | 6/2012 | DeWaard |

FOREIGN PATENT DOCUMENTS

| | | | |
|---|---|---|---|
| CA | 2719630 | 5/2011 | |
| CA | 2732065 | 8/2011 | |
| CA | 2737609 | 10/2011 | |
| CA | 2764679 | 7/2012 | |
| WO | WO 2010094115 A1 * | 8/2010 | ........... B01D 61/145 |

* cited by examiner

ANAEROBIC DIGESTING SYSTEMS AND METHODS FOR PROCESSING ANIMAL WASTE

RELATED APPLICATIONS

This application, U.S. patent application Ser. No. 13/592,170 filed Aug. 22, 2012, claims priority to U.S. Provisional Patent Application Ser. No. 61/526,617, filed Aug. 23, 2011.

TECHNICAL FIELD

The present invention relates to manure processing systems and methods for use in dairy operations and, more specifically, to anaerobic digesters, including anaerobic digesters used by waste processing systems and methods for use with dairy facility flush systems.

BACKGROUND

Dairy and similar livestock operations generate animal waste. The present invention is of particular significance in the field of dairy operations, and the invention will be described in the context of a dairy operation. The present invention may, however, have application to other environments.

In a dairy operation, cows are often held for periods of time in contained locations. Over time, cow waste collects in such contained locations and must be removed. Dairy systems thus typically use a flush system to remove cow waste from contained locations where the waste has collected. A flush system employs a pressurized liquid that is flushed onto the contained locations to remove the waste. The flush liquid and animal waste from a waste slurry that is collected and removed from the contained location.

The flush system thus requires both a continuous supply of flush liquid and a way to handle the waste slurry. To deal with both problems, processing systems have been developed that process the waste slurry generated by the flush system to obtain useable manure and, in some situations, to extract from the waste slurry a liquid suitable for use as the flush liquid.

Systems and methods of processing waste slurry generated by flush systems are described in U.S. Pat. No. 7,306,731 to DeWaard and in U.S. Patent Application Ser. No. 61/417,387, and the contents of the DeWaard '731 patent and the '387 application are incorporated herein by reference. The waste processing systems described in the DeWaard '731 patent and '387 application employ an arrangement of settling and storage tanks and liquid/solid separators to obtain useable flush liquid and also to provide a supply of material suitable for use in a digester. The flush liquid may be re-used by a conventional flush system, while the digester process yields dry solid manure material that may be safely spread directly on soil as fertilizer and/or liquid that may be used as fertilizer.

An important component of waste processing systems such as those described in the DeWaard '731 patent and the '387 application is an anaerobic digester. The process implemented by the anaerobic digester employs organisms to convert the feed material into its useable byproducts. The organisms employed by an anaerobic digester perform optimally under a narrow set of operating conditions. Further, the digesting process takes from days to weeks depending on the feed material and the conditions within the digester. The anaerobic digester can thus be a significant bottleneck in waste processing systems such as those described in the DeWaard '731 patent and the '387 application.

The present invention may be implemented as improved anaerobic digesters and, in one example implementation of the principles of the present invention, to improved waste processing systems and methods for optimizing the processing of waste slurry such as the waste slurry generated by a dairy flush system.

SUMMARY

The present invention may be embodied as a digester system for digesting feed material comprises a digester tank, a thickener, and a seal system. The digester tank generates a first digested material and biogas from the feed material. The thickener is operatively connected to the digester tank to remove a second digested material from the feed material to alter a solid content of the feed material in the digester tank. The seal system substantially prevents the thickener from removing biogas from the feed material with the second digested material.

The present invention may also be embodied as a waste processing system for waste slurry, comprising a digester tank, a thickener, and a seal system. The digester tank contains feed material. The feed material comprises at least a portion of the waste slurry. The digester tank generates a first digested material and biogas from the feed material. The thickener is operatively connected to the digester tank to remove a second digested material from the feed material to alter a solid content of the feed material in the digester tank. The seal system substantially prevents the thickener from removing biogas from the feed material with the second digested material.

The present invention may also be embodied as a method of digesting feed material comprising the following steps. The feed material is arranged within a digester tank and combined with microorganisms within the digester tank to generate a first digested material and biogas from the feed material. A second digested material is removed from the feed material to alter a solid content of the feed material in the digester tank. Back pressure is applied on the second digested material removed from the feed material substantially to maintain biogas within the feed material.

DETAILED DESCRIPTION

Figure 1:
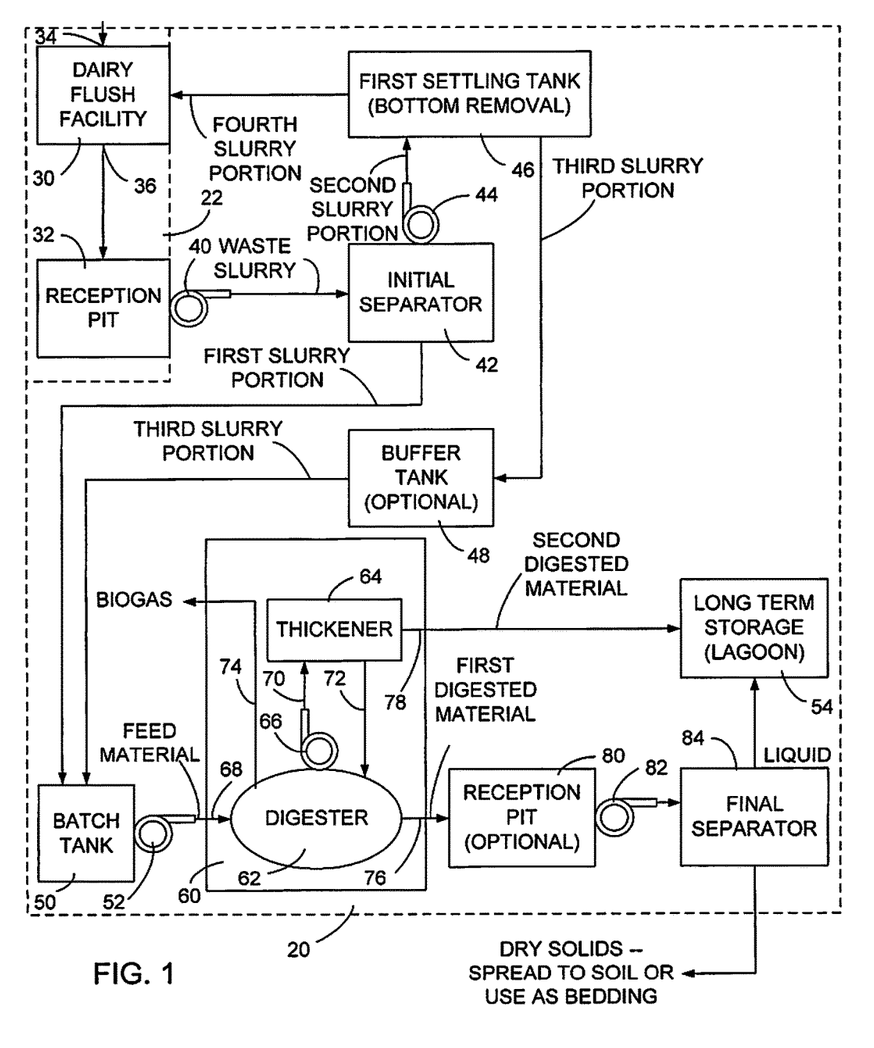
FIG. 1 is a schematic view of a first example manure processing system including an anaerobic digester system of the present invention.

Referring initially to FIG. 1 of the drawing, depicted therein is a first example waste processing system 20 adapted to be used with a flush system 22. The example flush system 22 is or may be conventional and comprises a dairy flush facility 30 and a reception pit 32. The flush facility 30 comprises an inlet 34 through which flush fluid is introduced and an outlet 36 through which waste slurry is collected. During use of the flush system 22, the flush liquid is mixed with animal waste and possibly additional contaminate material such as bedding material and animal feed to form waste slurry. The waste slurry flows through the outlet 36 and is collected in the reception pit 32.

The first example waste processing system 20 comprises a reception pit pump 40, a first or initial separator 42, a first separator pump 44, a first settling tank 46, an optional buffer tank 48, a batch tank 50, a batch tank pump 52, a long term storage facility or lagoon 54, and a primary anaerobic digester system 60. The anaerobic digester system 60 comprises a digester tank 62, a thickener system 64, an optional thickener pump 66, an inlet 68, and first, second, third, fourth, and fifth conduits 70, 72, 74, 76, and 78. The first and second conduits 70 and 72 allow fluid flow between the digester tank 62 and the thickener system 64. The third conduit 74 allows biogas to flow out of the digester tank 62. The long term storage facility or lagoon 54 allows long term storage of appropriate materials as will be described in further detail below. The example waste processing system 20 further comprises an optional reception pit 80, an optional reception pit pump 82, and a final separator 84. The fourth conduit 76 allows fluid to flow from the digester tank 62 to the final separator 84 through the optional reception pit 80, and the fifth conduit 78 allows fluid to flow from the thickener system 64 to the long term storage area or lagoon 48.

The waste processing system 20 operates basically as follows. The reception pit pump 40 pumps waste slurry from the reception pit 32 into the first separator 42. The first separator 42 causes a first portion of the waste slurry to flow into the batch tank 50, and the first separator pump 44 pumps a second portion of the waste slurry into the first settling tank 46. The first portion of the waste slurry is formed of what may be referred to as "solids" and comprises a mixture of liquid carrying solid biomass material suitable for processing using the digesting system 60. The second portion of the waste slurry comprises a mixture of liquid and a concentration of solid biomass material too low for effective processing using the digesting system 60.

The first settling tank 46 separates the second portion of the waste slurry into a third portion of the waste slurry that flows into the optional buffer tank 50 and a fourth portion of the waste slurry that flows into the dairy flush facility for reuse.

The third portion of the waste slurry comprises a mixture of liquid and solid biomass material suitable for processing using the digesting system 60. The liquid component of the third portion carries solid biomass material component of the third portion.

The fourth portion of the waste slurry comprises a mixture of liquids without sufficient concentrations of solid biomass material suitable for processing using the digesting system 60. To the contrary, the concentrations of biomass material in the fourth slurry portion are sufficiently low for the fourth slurry portion to be re-used as flush material by the dairy flush facility.

If used, the optional buffer tank 50 allows for storage of the third portion of the waste slurry as necessary during operation of the waste processing system 20. For example, the buffer tank 50 may be configured to store the third slurry portion while maintenance is performed on components of the waste processing system 20 downstream of the buffer tank 50 such as the anaerobic digester system 60. With or without the optional buffer tank 50, the batch tank 50 receives the first and second slurry portions from the first separator 42 and the first settling tank 46, respectively.

The first and third portions of the waste slurry are combined with make-up water to form a feed material appropriate for the digester system 60. The batch tank pump 52 forces the first digester mixture from the batch tank 50 into the digester tank 62 of the primary digester 60. In this application, the term "feed material" will be used to refer to the material within the digester system 60. In particular, feed material is stored within the example digester tank 62 and circulated through the example thickener 64. The characteristics (e.g., solids content) of the feed material may thus vary depending upon where within the digester system 60 the feed material is located. For example, a solids content of a thickened feed material passing through the conduit 72 will typically be higher than a solids content of a pre-thickened feed material passing through the conduit 70. And a solids content of the pre-thickened feed material passing through the conduit 70 will typically be similar to the average solids content of the feed material within the digester tank 62. Further, depending upon how well the feed material within the digester tank 62 is mixed, a solids content of the feed material within the digester tank 62 may vary from location to location within the digester tank 62, and such localized solids content values may differ slightly from the average solids content of the feed material within the digester tank 62.

The digester tank 62 mixes the feed material with microorganisms that, in the absence of oxygen, break down biodegradable material forming part of the feed material. In particular, in the example anaerobic digester system 60, the microorganisms break the biodegradable material in the digester tank 62 down into a biogas and a first digested material. The biogas from the digester tank 62 may be further processed to obtain useable energy. In the first example processing system 20, the first digested material is allowed to flow into the optional reception pit 80 for storage.

The final separator 84 allows a liquid portion of the final digested material to flow into the long term storage area or lagoon 48. The final separator 84 further yields dry solids that may be disposed of by, for example, being spread directly on soil or used as bedding material. If the reception pit 80 is used, the reception pit pump 82 forces the first digested material into the final separator 84.

Referring now more specifically to the example anaerobic digester system 60, FIG. 1 shows that the optional pump 66 forces fluid from the digester tank 62 to the thickener system 64 through the first conduit 70 and back from the thickener system 64 through the second conduit 72 to the digester tank 62. In general, the purpose of the thickener system 64 is to alter a solid content of the feed material within the digester system 60 such that the solid content is maintained within an optimal range or at an optimal value for the operating conditions of the digester tank 62. Additionally, the example thickener system 64 processes feed material flowing therethrough in a fluid-tight manner so any biogas contained with the processed material is returned to the digester tank 62. And as will be described in further detail below, the example digester system 60 removes liquids from the digester tank 62 at a faster rate than the solids such that the retention times of both portions is optimized.

More specifically, biodegradable material within a typical digester system may be characterized as having a solids portion and a hydraulic portion. The term "solids portion" may be used to refer to the solids within the feed material above a certain size, and the term hydraulic portion refers to a mixture of water, waste liquids, and suspended particulate solids that are smaller than the solids forming in what is referred to as the solids portion. The period of time that a biodegradable material must be held within a digester tank to allow the microorganisms to break the biodegradable material down will be referred to herein as the retention time. Under any conditions, the retention time associated with the solid portion is typically much longer than the retention time associated with the hydraulic portion. As one example, where the microorganisms might break down hydraulic materials in a period of approximately 3-5 days, the microorganisms might take a period of approximately 30-50 days to break down solid materials.

The Applicant has recognized that the operation of the digester tank 62 may be optimized by continuously removing the liquids form the feed material within the digester system 60 using the thickener system 64. By continuously removing liquids, the thickener system 64 prevents liquids (e.g., hydraulic portion) from being processed for longer than necessary. By returning the solids to the digester tank 62, the thickener allows the solids to remain within the digester tank 62 for as long as is necessary to break the solids down into the first digested material and the biogas. Accordingly, a digester system 60 having the thickener system 64 allows the digester tank 62 to be made smaller, allows biogas to be extracted from material within the digester system 60 more efficiently, results in a more complete digestion process, and makes better use of the digester tank 62. In addition, because the entire digester system 60, including both the digester tank 62 and the thickener system 64, is sealed, biogas is removed from the system 60 only from the digester tank 62 (e.g., through the conduit 74) and not inadvertently in the thickener system 64 during the thickening process.

Figure 2:
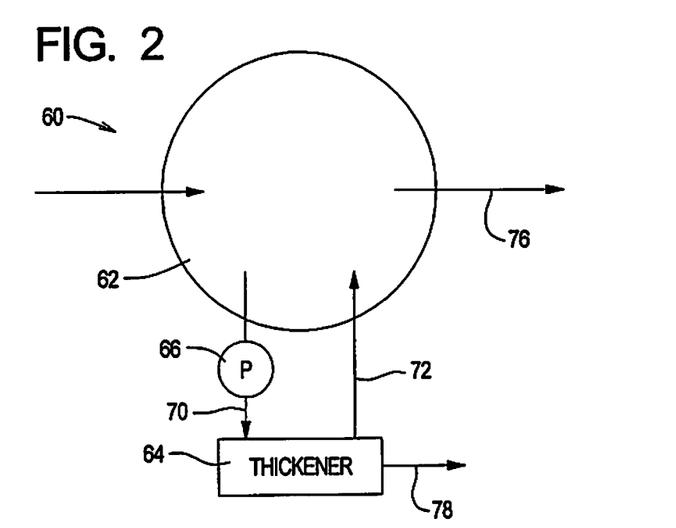
FIG. 2 is a somewhat schematic, top plan view of a first example anaerobic digester system that may be used in the example manure processing system of FIG. 1.
Figure 3:
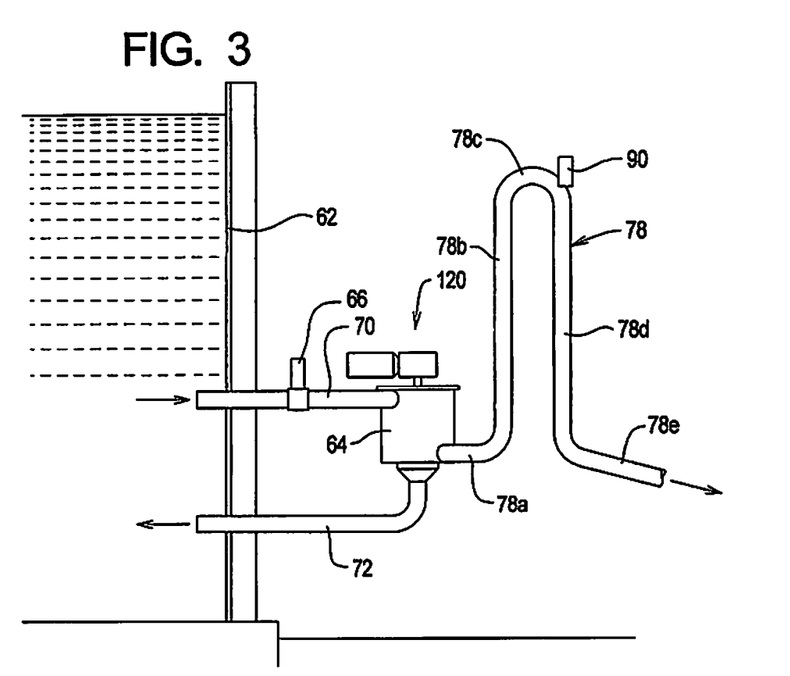
FIG. 3 is a side elevation view depicting the connection of a thickener system to a digesting tank of the example anaerobic digester system of FIG. 2.

Referring now to FIGS. 2-6 of the drawing, the example digester system 60 will now be described in further detail. FIG. 2 is a top plan view and FIG. 3 is a side elevation view illustrating the digester tank 62, the thickener system 64, and the conduits 70, 72, 76, and 78 arranged to form a complete mix digester system. As shown in FIG. 3, the fifth conduit 78 defines an inlet portion 78a, a first upright portion 78b, a corner portion 78c, a second upright portion 78d, and an outlet portion 78e. A vacuum break 90 is arranged on the corner portion 78c adjacent to the second upright portion 78d.

The example fifth conduit 78 forms at least part of what may be referred to as a seal system that ensures that the discharge from the thickener system 64 is always flooded. The corner portion 78c of the seal conduit 78 is arranged above the thickener system 64 and just under the level of feed material within the digester tank 62, and the vacuum break 90 ends just above the level of feed material within the digester tank 62. This arrangement allows the thickener system 64 to remove a liquid portion (e.g., first digested material) of the feed material circulating between the digester tank 62 and the thickener system 64 but substantially prevents biogas entrained within the feed material from exiting the digester system 60 with the liquid portion extracted by the thickener system 64.

Figure 4:
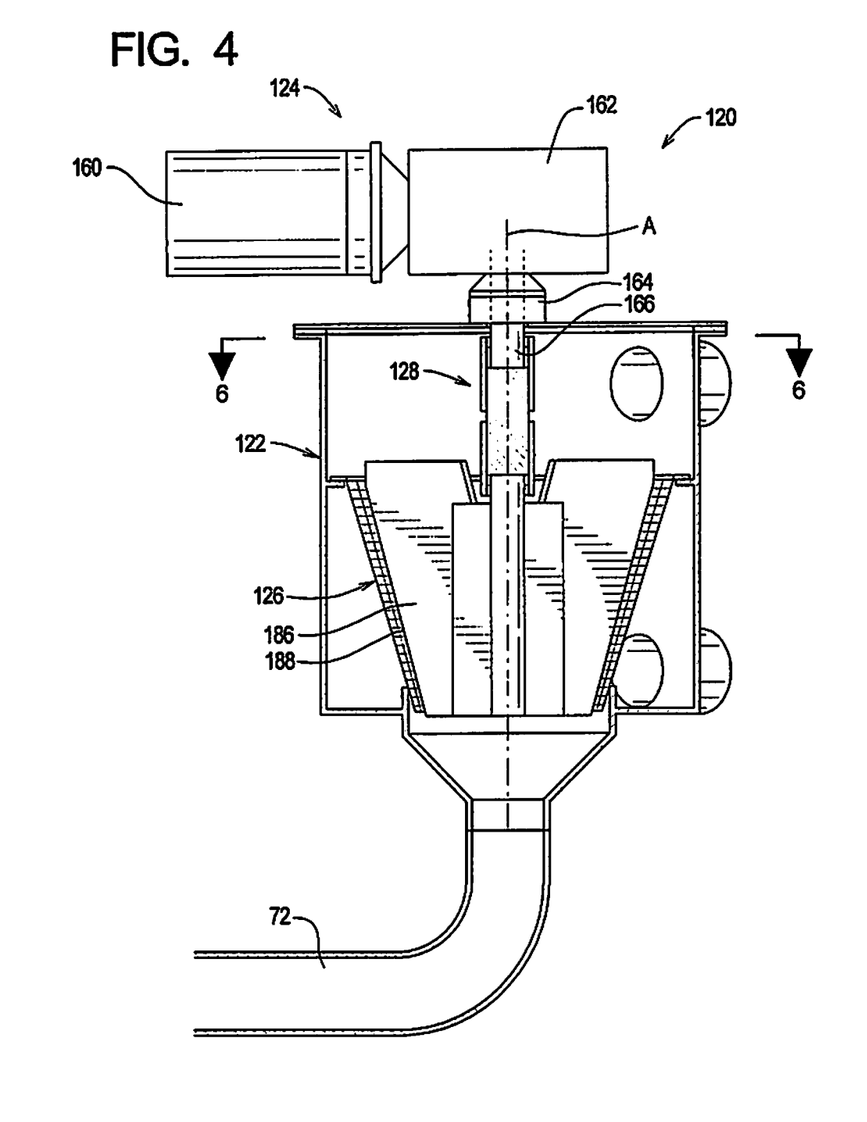
FIG. 4 is a side elevation, partial cutaway view of the thickener system depicted in FIG. 3.
Figure 5:
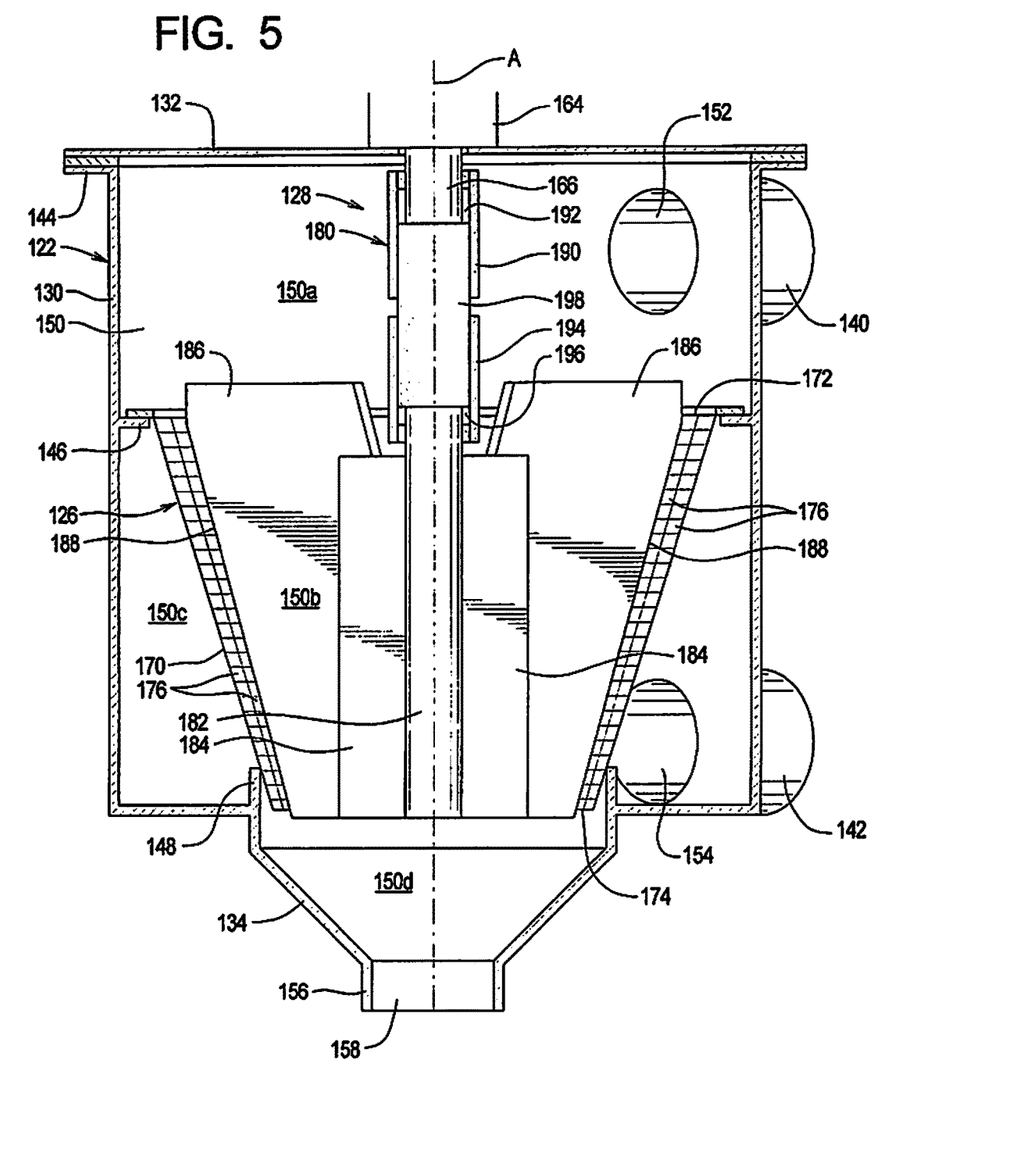
FIG. 5 is a side elevation cutaway view of the separator assembly of the thickener system depicted in FIG. 3.

FIGS. 3 and 4 illustrate that the example thickener system 64 comprises a thickener assembly 120. As perhaps best shown in FIG. 4, the example thickener assembly 120 comprises a housing assembly 122, a motor assembly 124, a screen structure 126, and a paddle assembly 128. FIG. 5 illustrates that the example housing assembly 122 comprises a housing member 130, a cover member 132, and a sump member 134. The housing member 130 comprises an inlet fitting 140, an outlet fitting 142, a cover support flange 144, an upper screen support flange 146, and a lower screen support flange 148. In the example housing assembly 122, the cover member 132 is supported on the housing member 130 by the cover support flange 144 to define a housing chamber 150. The inlet fitting 140 defines an inlet opening 152, while the outlet fitting 142 defines an outlet opening 154. The sump member 134 is secured to the housing member 130 below the lower screen support flange 148 and comprises a sump fitting 156 defining a sump opening 158.

FIG. 4 illustrates that the example motor assembly 124 comprises a motor 160 and a transmission 162 from which extends a mounting bearing 164 and a drive shaft 166. As perhaps best shown in FIG. 5, in the example thickener assembly 120 the mounting bearing 164 engages the cover member 132 such that the drive shaft 166 extends through the cover member 132 and into the housing chamber 150.

FIG. 5 further shows that the example screen structure 126 comprises a wall 170. The wall 170 is frusto-conical and defines a first, larger opening 172 and a second, smaller opening 174. FIG. 5 also shows that the frusto-conical wall 170 of the screen structure 126 is perforated to define a plurality of screen apertures or openings 176. In the example thickener assembly 120, the screen structure 126 is supported within housing chamber 150 by the upper and lower screen support flanges 146 and 148. When supported within the housing chamber 150, the screen structure 126 defines an inlet portion 150a of the housing chamber 150 above the first opening 172 of the screen structure 126, a working portion 150b of the housing chamber 150 within the wall 170 of screen structure 126, an outlet portion 150c of the housing chamber 150 outside of the wall 170 of the screen structure 126, and a sump portion 150d below the second opening 174 of the screen structure 126.

Further, FIG. 5 illustrates that, in the example thickener assembly 120, the inlet opening 152 is in fluid communication with the housing chamber inlet portion 150a, the outlet opening 154 is in fluid communication with the chamber outlet portion 150c, and the sump opening 158 is in fluid communication with the chamber sump portion 150d. Fluid may also pass from the chamber inlet portion 150a to the chamber working portion 150b through the first opening 172 and from the chamber working portion 150b to the chamber sump portion 150d through the second opening 174. Finally, as will be described in further detail below, fluid may also pass from the chamber working portion 150b to the chamber outlet portion 150c through the screen openings 176. As generally discussed above, the housing assembly 122 is sealed such that biogas entrained within the feed material flowing through the housing chamber 150 does not escape.

Figure 6:
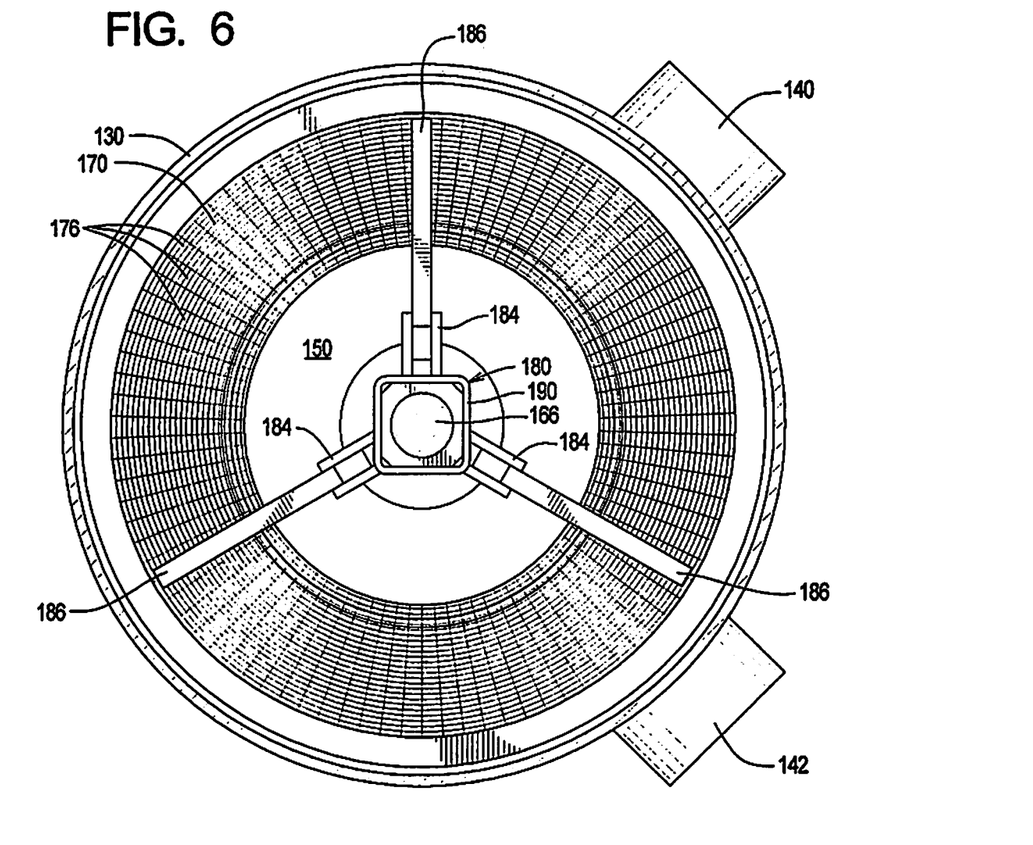
FIG. 6 is a top plan view of the separator assembly taken along lines 6-6 in FIG. 4.

Turning now to the paddle assembly 128, FIGS. 5 and 6 illustrate that the example paddle assembly 128 comprises a coupling assembly 180, a shaft 182 defining a plurality of paddle supports 184, and a plurality of paddle members 186 attached to and supported by the paddle supports 184. The paddle members 186 each define a working edge surface 188. As perhaps best shown with reference to FIGS. 5 and 6, the paddle supports 184 engage the paddle members 186 such that working edge surfaces 188 are radially spaced from the vane shaft 182. And as shown in FIGS. 4 and 5, working edge surfaces 188 are angled such that, with the paddle members 186 supported by the paddle supports 184, the working edges 188 lie substantially within a conical reference shape. Further, the conical reference shape of the working edges 188 substantially conforms to the frusto-conical shape of the wall 170 of the screen structure 126. The example paddle assembly 128 comprises three of the paddle members 186 as shown in FIG. 6, but any number of paddle members 186 may be provided. Further, the paddle members 186 may be made of any material compatible with the feed material and capable of structurally operating as generally described herein, with metal and/or plastic being suitable materials.

FIG. 5 perhaps best shows that the coupling assembly 180 comprises a first coupler housing 190 defining a first coupler chamber 192, a second coupler housing 194 defining a second coupler chamber 196, and a coupler member 198. The first coupler housing 190 is rigidly connected to the drive shaft 166, and the second coupler housing 194 is rigidly connected to the vane shaft 182. The coupler member 198 is sized and dimensioned to fit within the first and second coupler chambers 192 and 196. And as shown in FIG. 6, a cross-sectional area of the coupler member 198 is non-circular and is substantially the same as a cross-sectional area of the first and second coupler chambers 192 and 196. In the example coupling assembly 180, the cross-sectional areas of the coupler chambers 192 and 196 are rectangular or square and slightly larger than the cross-sectional area of the coupler member 198. Other shapes in addition to rectangular or square and appropriate tolerances can be used, however.

The coupling assembly 180 thus transfers rotational movement of the drive shaft 166 to the vane shaft 182 but allows longitudinal movement of the coupler member 198 relative to the housing members 190 and 194. Therefore, the working edges 188 of the paddle members 186 are held in contact by gravity with the wall 170 of the screen structure 126.

As shown in FIG. 5, when the example housing assembly 122, the example motor assembly 124, the example screen structure 126, and the example paddle assembly 128 are assembled to define the thickener assembly 120, the longitudinal axes of the drive shaft 166, the frusto-conical wall 170, and the vane shaft 182 are all aligned along a system axis A. Axial rotation of the drive shaft 166 about the system axis A causes axial rotation of the vane shaft 182 which in turn causes the vanes 186 to rotate about the system axis A such that the working edges 188 scrape along an interior surface of the screen wall 170. Further, because gravity holds the vane working edges 188 in contact with the screen wall 170, these working edges 188 stay in contact with the screen wall 170 as they wear because the coupling assembly 180 allows the vane shaft 182 to move relative to the drive shaft 166 along the system axis A.

The thickener system assembly 120 operates basically as follows. The first, second, and fifth conduits 70, 72, and 78 are connected to the inlet fitting 140, the outlet fitting 142, and the sump fitting 156, respectively, in a fluid-tight manner. Gravity and/or operation of the optional thickener pump 66 causes fluid within the digester tank 62 to flow into the thickener assembly 120 through the first conduit 70. The fluid flowing through the first conduit 70 comprises liquids (hydraulic portion), solids (solid portion), and possibly gasses (entrained biogases).

The fluid flowing through the first conduit 70 initially enters the inlet portion 150a of the housing chamber 150 defined by the housing assembly 122. The fluid in the inlet portion 150a then flows through the first opening 172 defined by the screen structure 126 and into the working portion 150b of the housing chamber 150. At the same time, the motor assembly 124 is operated to cause axial rotation of the drive shaft 166 and thus (through the coupling system 180 and vane shaft 182) circular revolution of the paddle members 186 about the system axis A. As the paddle members 186 revolve about the system axis A, the working edges 188 displace at least a portion of the fluid within the working chamber portion 150b along the wall 170 of the screen structure 126. This action of the working edges 188 against the wall 170 allows primarily a liquid (hydraulic) portion of the fluids within the working chamber portion 150b to flow through the screen openings 176 in the screen structure wall 170 and into the chamber outlet portion 150c.

In particular, the working edges 188 scrape any solids from the screen structure wall 170 to ensure that liquids are allowed to flow through the apertures or openings 176. The fluid within the outlet chamber portion 150c is what was referred to above as the second digested material and flows through the fifth conduit 78 into the long term storage area (lagoon) 48. As shown in FIG. 3, the example corner portion 78c of the fifth conduit 78 is above the thickener 64 and below a level of the material within the digester tank 62. Fluid within the first upright portion 78b of the fifth conduit 78 thus maintains back pressure on the fluid flowing through the housing chamber 150 to control a rate of flow of the fluid through the housing chamber 150 and out of the outlet fitting 142 and into the fifth conduit 78. When the thickener system 64 is not working, the liquid feed material is prevented from exiting the thickener 64 by hydraulic pressure.

Any fluid within the second or working chamber portion 150b not forced through the screen openings 176 eventually flows out of the working chamber portion 150b through the second opening 174 defined by the screen structure 126, into the sump chamber portion 150d, out of the sump opening 158, through the second conduit 72, and back into the digester tank 62. Similarly, most biogases entrained within the liquids flowing through the working portion 150b of the housing chamber 150 will not flow through the screen structure wall 170 but will instead be entrained by fluid flowing through the sump chamber portion 150d and out of the sump opening 158 and thus will be returned to the digester tank 62.

From the foregoing, it should be clear that the thickener assembly 120 thus extracts some of the liquid from the fluid material flowing housing chamber 150. The amount of liquid extracted by the thickener assembly 120 depends upon factors such as flow rate of material through the thickener 120, the percent of solid in the material entering the thickener assembly 120, the speed at which the paddle members 186 revolve about the system axis A, and the size, shape, and/or orientation of the screen structure 126 and/or the screen openings 176 therein.

In one example implementation of the digester system 60, the material entering the digester tank 62 comprises approximately 3% solids by volume. In this example, the material entering the thickener 64 comprises approximately 8.0% solids by volume and material leaving the thickener 64 comprises approximately 8.5% solids by volume. Under these conditions, the thickener 64 is configured to remove approximately 6.25% of the liquids in the material flowing through the thickener 64. More generally, the thickener 64 should remove a first range of approximately 5.5% to 7.25%, by volume, of the fluids from the material flowing through the thickener 64 and should, in any event, remove a second range of approximately 4% to 10.0%, by volume, of the fluids from the material flowing through the thickener 64. These numbers are by way of example only. The exact parameters will depend on factors including the nature of the feed material and the size and operating conditions of the digester tank 62.

In an example implementation of the digester system 60, the inlet port 152 of the thickener 64 is located a depth distance below a fluid level of the material within the digester tank 62. The depth distance is predetermined to maintain a sufficient back pressure on the fluid flowing through the outlet port 154 of the thickener 64 for proper circulation of material between the digester tank 62 and the thickener 64 as described herein.

Figure 7:
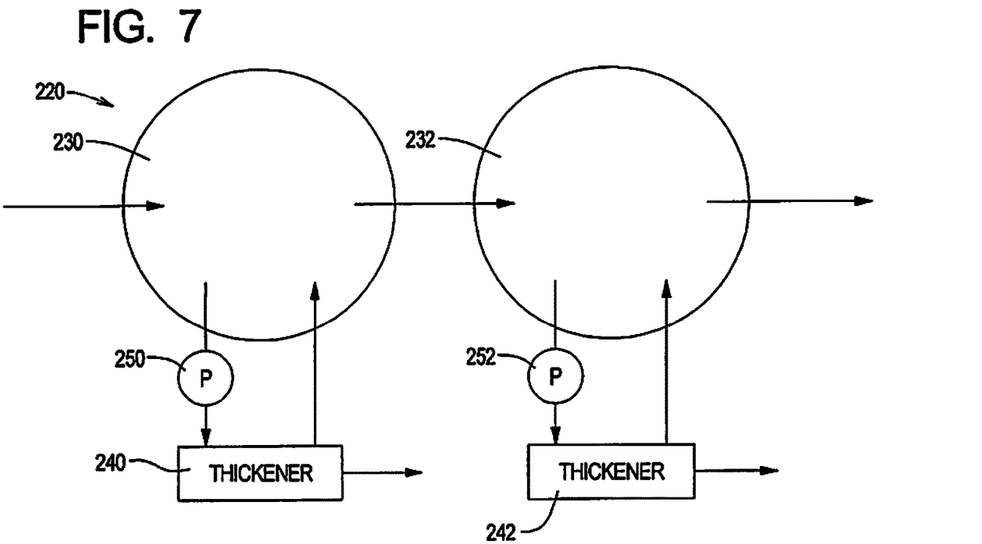
FIG. 7 is a somewhat schematic, top plan view of a second example anaerobic digester system that may be used in the example manure processing system of FIG. 1.

Referring now to FIG. 7 of the drawing, depicted therein is a second example digester system 220 that may be used in place of the example digester system 60 in the waste processing system 20 described above. The second example digester system 220 comprises first and second digester tanks 230 and 232, first and second thickeners 240 and 242, and, optionally, first and second thickener pumps 250 and 252. In this second example digester system 220, the first and second digester tanks 230 and 232 are complete mix digesters arranged in series.

The exact parameters of the second example digester 220 will depend on factors such as the nature of the feed material.

Figure 8:
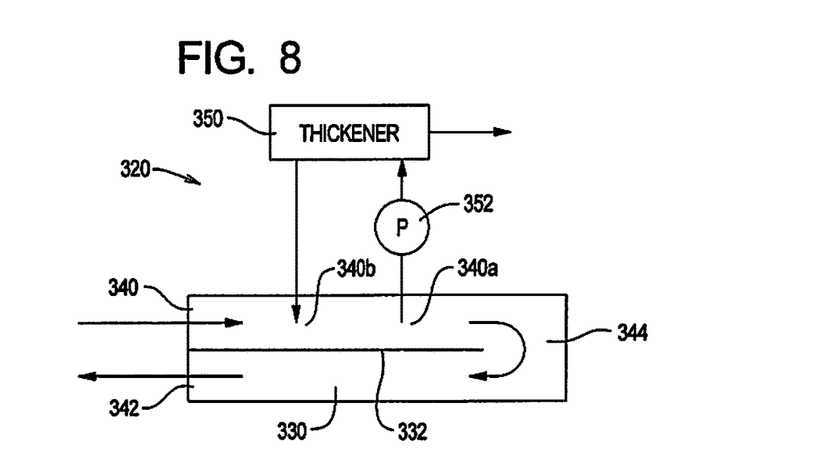
FIG. 8 is a somewhat schematic, top plan view of a third example anaerobic digester system that may be used in the example manure processing system of FIG. 1.

Referring now to FIG. 8 of the drawing, depicted therein is a third example digester system 320 that may be used in place of the example digester system 60 in the waste processing system 20 described above. The third example digester system 320 is a plug flow digester and comprises a digester tank 330 comprising a baffle wall 332. The baffle wall 332 defines an inlet portion 340, an outlet portion 342, and an intermediate portion 344. Material flowing through the digester tank 330 flows initially through the inlet portion 340, then through the intermediate portion 344, and then through the outlet portion 342. The third example digester system 320 further comprises a thickener 350 and a thickener pump 352. The thickener pump 352 is arranged to remove material from a first portion 340*a* of the inlet portion 340, and the thickener 350 is arranged to place material into a second portion 340*b* of the inlet portion 340. The first inlet portion 340*a* is downstream of the second inlet portion 340*b*.

The exact parameters of the third example digester system 320 will depend on factors such as the nature of the feed material.

Figure 9:
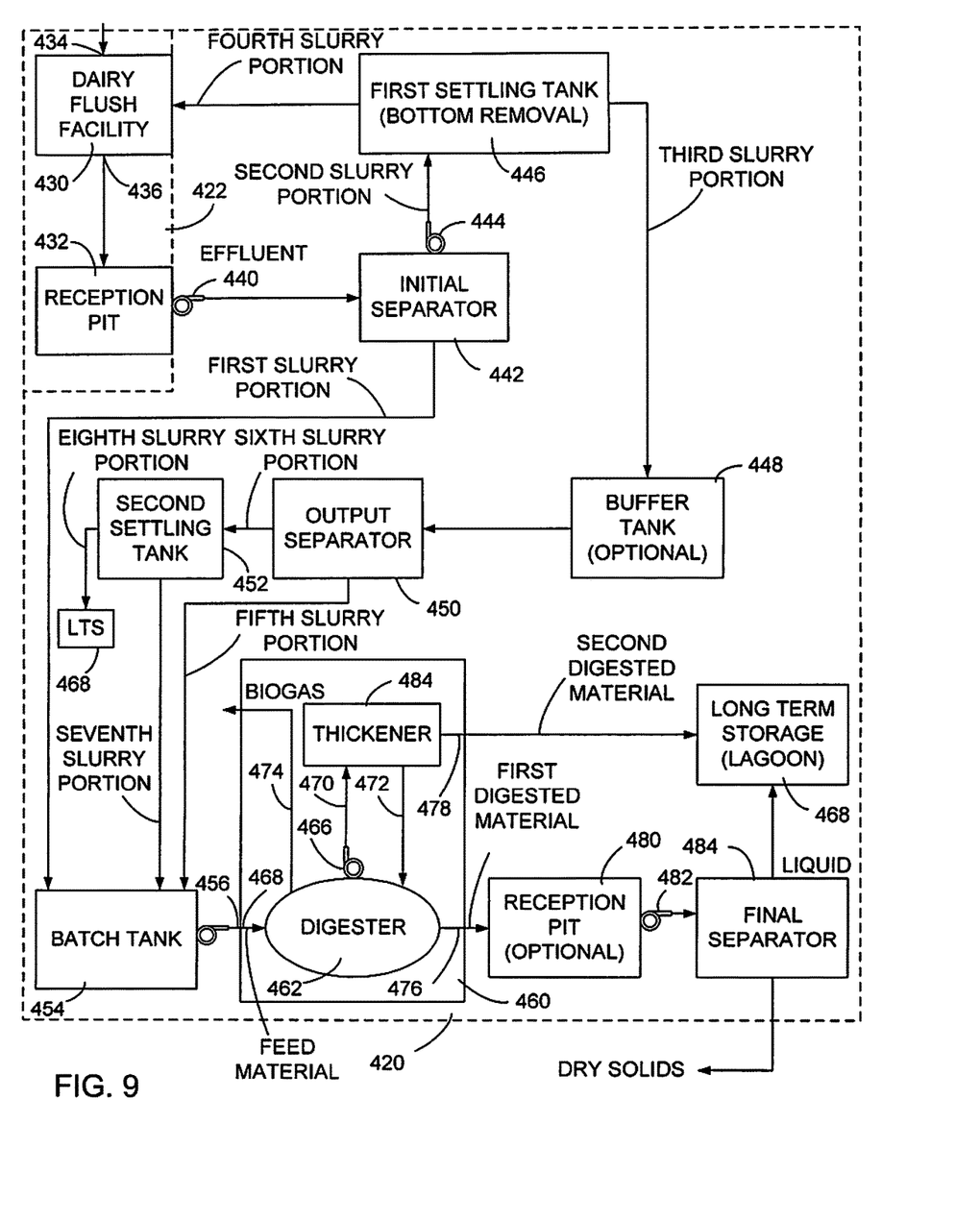
FIG. 9 is a schematic view of a second example manure processing system including an anaerobic digester system of the present invention.

Referring now to FIG. 9 of the drawing, depicted therein is a second example waste processing system 420 adapted to be used with a flush system 422. The example flush system 422 is or may be conventional and comprises a dairy flush facility 430 and a reception pit 432. The flush facility 430 comprises an inlet 434 through which flush fluid is introduced and an outlet 436 through which waste slurry is collected. During use of the flush system 422, the flush liquid is mixed with animal waste and possibly contaminate material such as bedding material and animal feed to form waste slurry. The waste slurry flows through the outlet 436 and is collected in the reception pit 432.

The waste processing system 420 comprises a reception pit pump 440, a first or initial separator 442, a first separator pump 444, a first settling tank 446, an option buffer tank 448, an output separator 450, a second settling tank 452, a batch tank 454, a batch tank pump 456, and a primary anaerobic digester system 460. The anaerobic digester system 460 comprising a digester tank 462, a thickener system 464, an optional thickener pump 466, and an inlet 468. A conventional long term storage facility (lagoon) 468 may be provided for long term storage of appropriate materials as will be described in further detail below.

First and second conduits 470 and 472 allow fluid flow between the digester tank 462 and the thickener system 464. A third conduit 474 allows biogas to flow out of the digester tank 462. The example waste processing system 420 further comprises an optional reception pit 480, an optional reception pit pump 482, and a final separator 484. A fourth conduit 476 allows fluid to flow from the digester tank 462 to the final separator 484 through the optional reception pit 480, and a fifth conduit 478 allows fluid to flow from the thickener system 464 to the long term storage area or lagoon 448.

Like the example first conduit 78 described above, the example fifth conduit 478 forms at least part of what may be referred to as a seal system that ensures that the discharge from the thickener system 464 is always flooded. In particular, like the example first conduit 78, the example fifth conduit 478 may be configured to define a corner portion arranged just under the elevation of feed material within the digester tank 462, and a vacuum break may be arranged in the corner portion to end just above the level of feed material within the digester tank 462. This arrangement allows the thickener system 464 to remove a liquid portion (e.g., first digested material) of the feed material circulating between the digester tank 462 and the thickener system 464 but substantially prevents biogas entrained within the feed material from exiting the digester system 460 with the liquid portion extracted by the thickener system 464.

The example waste processing system 420 operates basically as follows. The reception pit pump 440 pumps waste slurry from the reception pit 432 into the first separator 442. The first separator 442 causes a first portion of the waste slurry to flow into the batch tank 454, and the first separator pump 444 pumps a second (effluent) portion of the waste slurry into the first settling tank 446. The first portion of the waste slurry is formed of what is referred to as "solids" and comprises a mixture of liquid carrying a sufficiently high concentration of solid biomass material suitable for processing using the digesting system 460. The second portion of the waste slurry is a mixture of liquids and a relatively low concentration of solid biomass; the second slurry portion is not well-suited for processing using the digesting system 460 and thus is caused to flow into the first settling tank 446.

The first settling tank 446 causes a third portion of the waste slurry to flow into the output separator 450 and a fourth portion of the waste slurry to flow back into the dairy flush facility 430 for reuse. If the optional buffer tank 448 is used, the third portion of the waste slurry flows through the buffer tank 448 before flowing into the output separator 450. The optional buffer tank 448 allows for storage of the third portion of the waste slurry as necessary during operation of the waste processing system 420. The third portion of the waste slurry is formed of a higher concentration of "solids" and comprises a mixture of liquid carrying solid biomass material suitable for processing using the digesting system 460. The fourth portion of the waste slurry comprises a mixture of liquids without appreciable quantities of solid biomass material suitable for processing using the digesting system 460.

The output separator 450 processes the third slurry portion to obtain a fifth slurry portion and a sixth slurry portion. The fifth slurry portion primarily comprises a relatively high concentration of biomass suitable for processing by the digester 460 and flows directly into the batch tank 454. The sixth slurry portion comprises a mixture of liquids with a relatively low concentration of solids. The sixth slurry portion flows into the second settling tank 452. The second settling tank 452 is a bottom removal system that separates the sixth slurry portion into seventh and eighth slurry portions. The seventh slurry portion comprises a mixture of liquids with a relatively high concentration of biomass suitable for processing by the digester 460 and thus flows directly into the batch tank 454. The eighth slurry portion comprises a mixture of liquids with a sufficiently low concentration of solids that the eighth slurry portion is allowed to flow directly to the long term storage facility 468.

The batch tank 454 receives the first, fifth, and seventh slurry portions from the first separator 442, the output separator 450, and the second settling tank 452, respectively. The first, fifth, and seventh portions of the waste slurry are combined with make-up water to form a feed material appropriate for the digester system 460. The batch tank pump 456 forces the first digester mixture from the batch tank 454 into the digester tank 462 of the primary digester 460. The digester tank 462 mixes the feed material with microorganisms that, in the absence of oxygen, break down biodegradable material forming part the feed material. In particular, in the example anaerobic digester system 460, the microorganisms break the solid biomass material in the digester tank 462 down into a biogas and first and second digested materials. The biogas from the digester tank 462 may be further processed to obtain useable energy.

The first digested material may be allowed to flow directly into the final separator 484 or, optionally, into the reception pit 480 for storage. If the reception pit 480 is used, the reception pit pump 482 forces the first digested material into the final separator 484. With or without the reception pit 480, the final separator 484 allows a liquid portion of the final digested material to flow into the long term storage facility or lagoon 468. The final separator 484 further yields dry solids that may be disposed of by, for example, being spread directly on soil or used as bedding material.

Referring now more specifically to the example anaerobic digester system 460, FIG. 9 shows that the optional pump 466 forces fluid from the digester tank 462 to the thickener system 464 through the first conduit 470 and back from the thickener system 464 through the second conduit 472 to the digester tank 462. In general, the purpose of the thickener system 464 is to alter a solid content of the material within the digester system 460 such that the solid content is maintained within an optimal range or at an optimal value for the operating conditions of the digester tank 462. Additionally, the example thickener system 464 processes material flowing therethrough in a fluid-tight manner so any biogas contained with the processed material is returned to the digester tank 462. And as will be described in further detail below, the thickener system 464 also continually removes a small portion of the relatively fast digesting liquid material (hydraulic portion) from the digester system 460 in the form of the second digested material and thus improves operating efficiency of the overall system 460.

Biodegradable material within a typical digester system may be characterized as having a solids portion and a hydraulic portion. The period of time that a biodegradable material must be held within a digester tank to allow the microorganisms to break the biodegradable material down will be referred to herein as the retention time. Under any conditions, the retention time associated with the solid portion is typically much longer than the retention time associated with the hydraulic portion. As one example, where the microorganisms might break down hydraulic materials in a period of approximately 3-5 days under a given set of digesting conditions, the microorganisms might take a period of approximately 30-50 days to break down solid materials under that same set of digesting conditions.

Again, the Applicant has recognized that the operation of the digester tank 462 may be optimized by using the thickener system 464 continuously to remove liquids, and thus the quick-digesting hydraulic portion, from the material within the digester system 460. By continuously removing liquids, the thickener system 464 prevents liquids from being processed for longer than necessary. By returning the solids to the digester tank 462, the thickener allows the solids to remain within the digester tank 462 for as long as is necessary to break the solids down into the first digested material and the biogas. Accordingly, a digester system 460 having the thickener system 464 the digester tank 462 to be made smaller, allows biogas to be extracted from material within the digester system 460 more efficiently, results in a more complete digestion process, and makes better use of the digester tank 462. In addition, because the entire digester system 460, including both the digester tank 462 and the thickener system 464, is sealed, biogas is removed from the system 460 only from the digester tank 462 and not inadvertently in the thickener system 464 during the thickening process.

The example digester system 460 of the example waste processing system 420 may be constructed and used in the same manner as the example digester system 60 described above and will not be described in further detail herein.

Figure 10:
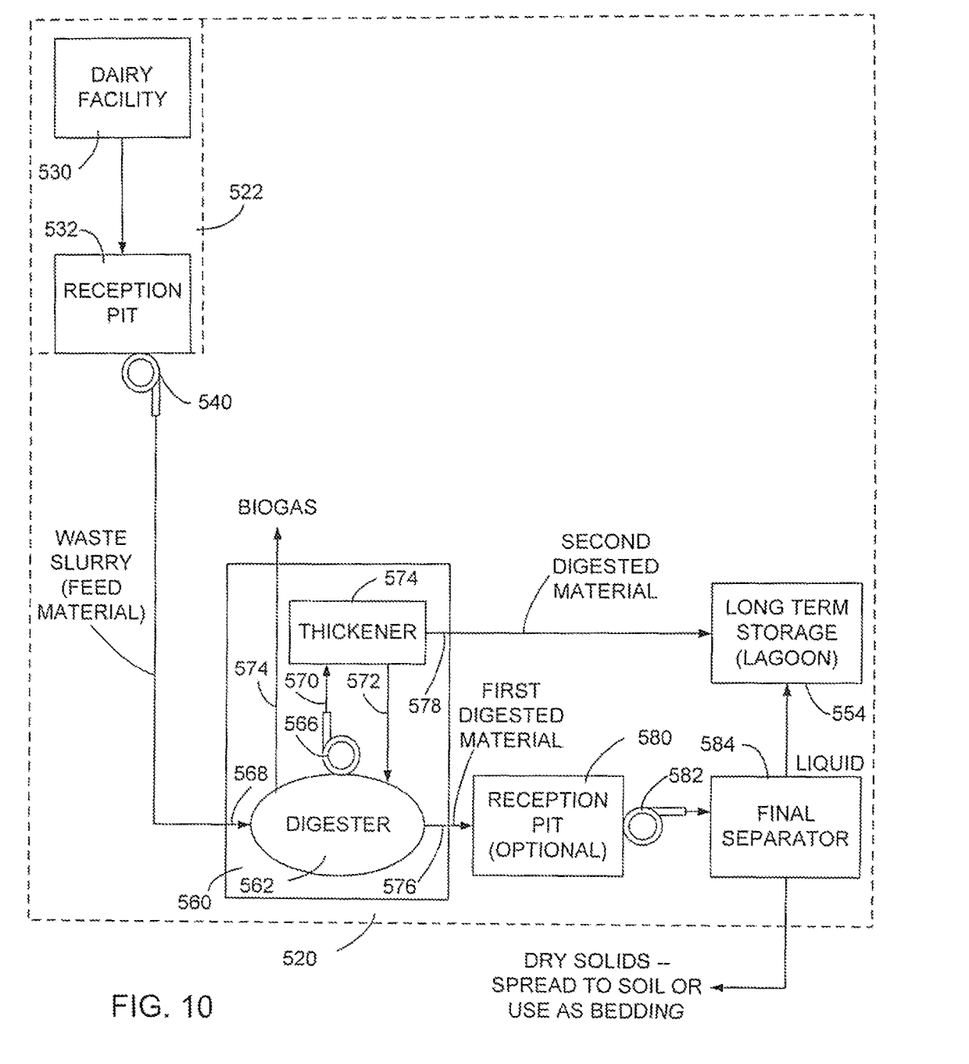
FIG. 10 is a schematic view of a third example manure processing system including an anaerobic digester system of the present invention.

Referring now to FIG. 10 of the drawing, depicted therein is a third example waste processing system 520 adapted to be used with a scrape system 522. The example dairy scrape system 522 is or may be conventional and comprises a dairy facility 530 and, optionally, a reception pit 532. During use of the dairy scrape system 522, animal waste and possibly additional contaminate material such as bedding material and animal feed are removed to form waste slurry that is collected in the reception pit 532 in the example waste processing system 520.

The third example waste processing system 520 comprises a reception pit pump 540 and a primary anaerobic digester system 560. The anaerobic digester system 560 comprises a digester tank 562, a thickener system 564, an optional thickener pump 566, an inlet 568, and first, second, third, fourth, and fifth conduits 570, 572, 574, 576, and 578. The first and second conduits 570 and 572 allow fluid flow between the digester tank 562 and the thickener system 564. The third conduit 574 allows biogas to flow out of the digester tank 562. The long term storage facility or lagoon 548 allows long term storage of appropriate materials as will be described in further detail below. The example waste processing system 520 further comprises an optional reception pit 580, an optional reception pit pump 582, and a final separator 584. The fourth conduit 576 allows fluid to flow from the digester tank 562 to the final separator 584 through the optional reception pit 580, and the fifth conduit 578 allows fluid to flow from the thickener system 564 to the long term storage area or lagoon 548.

Like the example first conduit 78 described above, the example fifth conduit 578 forms at least part of what may be referred to as a seal system that ensures that the discharge from the thickener system 564 is always flooded. In particular, like the example first conduit 78, the example fifth conduit 578 may be configured to define a corner portion arranged just under the elevation of feed material within the digester tank 562, and a vacuum break may be arranged in the corner portion to end just above the level of feed material within the digester tank 562. This arrangement allows the thickener system 564 to remove a liquid portion (e.g., first digested material) of the feed material circulating between the digester tank 562 and the thickener system 564 but substantially prevents biogas entrained within the feed material from exiting the digester system 560 with the liquid portion extracted by the thickener system 564.

The third example waste processing system 520 operates basically as follows. The reception pit pump 540 pumps waste slurry from the reception pit 532 directly into the digester system 560. Again, in this application the term "feed material" will be used to refer to the material within the digester system 560. In particular, feed material is stored within the example digester tank 562 and circulated through the example thickener 564. The characteristics (e.g., solids content) of the feed material may thus vary depending upon where within the digester system 560 the feed material is located. For example, a solids content of a thickened feed material passing through the conduit 572 will typically be higher than a solids content of a pre-thickened feed material passing through the conduit 570. And a solids content of the pre-thickened feed material passing through the conduit 570 will typically be similar to the average solids content of the feed material within the digester tank 562. Further, depending upon how well the feed material within the digester tank 562 is mixed, a solids content of the feed material within the digester tank 562 may vary from location to location within the digester tank 562, and such localized solids content values may differ slightly from the average solids content of the feed material within the digester tank 562.

The digester tank 562 mixes the feed material with microorganisms that, in the absence of oxygen, break down biodegradable material forming part of the feed material. In particular, in the example anaerobic digester system 560, the microorganisms break the biodegradable material in the digester tank 562 down into a biogas and a first digested material. The biogas from the digester tank 562 may be further processed to obtain useable energy. In the third example processing system 520, the first digested material is allowed to flow into the optional reception pit 580 for storage.

The final separator 584 allows a liquid portion of the final digested material to flow into the long term storage area or lagoon 548. The final separator 584 further yields dry solids that may be disposed of by, for example, being spread directly on soil or used as bedding material. If the reception pit 580 is used, the reception pit pump 582 forces the first digested material into the final separator 584.

Referring now more specifically to the example anaerobic digester system 560, FIG. 1 shows that the optional pump 566 forces fluid from the digester tank 562 to the thickener system 564 through the first conduit 570 and back from the thickener system 564 through the second conduit 572 to the digester tank 562. In general, the purpose of the thickener system 564 is to alter a solid content of the feed material within the digester system 560 such that the solid content is maintained within an optimal range or at an optimal value for the operating conditions of the digester tank 562. Additionally, the example thickener system 564 processes feed material flowing therethrough in a fluid-tight manner so any biogas contained with the processed material is returned to the digester tank 562. And as will be described in further detail below, the example digester system 560 removes liquids from the digester tank 562 at a faster rate than the solids such that the retention times of both portions is optimized.

More specifically, biodegradable material within a typical digester system may be characterized as having a solids portion and a hydraulic portion. The term "solids portion" may be used to refer to the solids within the feed material above a certain size, and the term hydraulic portion refers to a mixture of water, waste liquids, and suspended particulate solids that are smaller than the solids forming what is referred to as the solids portion. The period of time that a biodegradable material must be held within a digester tank to allow the microorganisms to break the biodegradable material down will be referred to herein as the retention time. Under any conditions, the retention time associated with the solid portion is typically much longer than the retention time associated with the hydraulic portion. As one example, where the microorganisms might break down hydraulic materials in a period of approximately 3-5 days, the microorganisms might take a period of approximately 30-50 days to break down solid materials.

The Applicant has recognized that the operation of the digester tank 562 may be optimized by continuously removing the liquids form the feed material within the digester system 560 using the thickener system 564. By continuously removing liquids, the thickener system 564 prevents liquids (e.g., hydraulic portion) from being processed for longer than necessary. By returning the solids to the digester tank 562, the thickener allows the solids to remain within the digester tank 562 for as long as is necessary to break the solids down into the first digested material and the biogas. Accordingly, a digester system 560 having the thickener system 564 allows the digester tank 562 to be made smaller, allows biogas to be extracted from material within the digester system 560 more efficiently, results in a more complete digestion process, and makes better use of the digester tank 562. In addition, because the entire digester system 560, including both the digester tank 562 and the thickener system 564, is sealed, biogas is removed from the system 560 only from the digester tank 562 (e.g., through the conduit 574) and not inadvertently in the thickener system 564 during the thickening process.

The example digester system 560 of the example waste processing system 520 may be constructed and used in the same manner as the example digester system 60 described above and will not be described in further detail herein.

The foregoing detailed description section of the present application discloses a number of examples of operating environments in which a digester system of the present invention may be used. It should be apparent that a digester system of the present invention may be used in other operating environments in which a digester is used to generate digested material and biogas. As additional examples, a digester system of the present invention may be used as part of any digester for which extension of solid retention time is desirable, such as a waste processing system for a dairy having a slip stream that normally goes to long term storage, a waste processing system for a dairy that does not employ a slip stream going to long term storage (e.g., manure enters the digester at around 4% solids and 8% solids is preferred), a waste processing system for a dairy in which solids are separated out first for other purposes and the digester is used primarily for the effluent, for a non-dairy digester having a very thin fraction, for a dairy of any type in which the feed material for the digester contains low solids, or any waste processing system with a high rate digester that retains solids to allow the digested liquid portion to be removed from the system.

What is claimed is:

1. A digester system for digesting feed material comprising liquids and solids, comprising:
   a digester tank, where the digester tank generates a first digested material and biogas from the feed material;
   a thickener;
   a first conduit operatively connected between the thickener and the digester tank to allow a pre-thickened feed material to flow from the digester tank to the thickener;
   a second conduit operatively connected between the thickener and the digester tank to allow a thickened feed material to flow from the thickener to the digester tank; and
   a seal conduit operatively connected to the thickener to allow a second digested material to flow out of the thickener; wherein
   the seal conduit defines a corner portion arranged above the thickener and below a level of the feed material within the digester tank such that the corner portion and the thickener are flooded with teed material substantially to prevent the thickener from allowing entrained biogas in the pre-thickened feed material from exiting the thickener with the second digested material.

2. A digester system as recited in claim 1, in which the seal conduit is configured to maintain back pressure on the second digested material flowing out of the thickener.

3. A digester system as recited in claim 1, further comprising a vacuum break arranged in the corner portion of the seal conduit.

4. A digester system as recited in claim 3, in which the vacuum break terminates above the level of feed material within the digester tank.

5. A digester system as recited in claim 1, in which the thickener maintains a solid content of the feed material in the digester tank within a predetermined range.

6. A digester system as recited in claim 1, further comprising a third conduit operatively connected to the digester tank, where the third conduit allows biogas to flow out of the digester tank.

7. A digester system as recited in claim 1, further comprising a thickener pump for causing at least a portion of the feed material to flow from the digester tank through the first conduit, through the thickener, and back into the digester tank through the second conduit.

8. A digester system as recited in claim 1, in which the thickener comprises a screen structure, where the second digested material flows through the screen structure and out of the thickener.

9. A digester system as recited in claim 8, in which the thickener further comprises:
   a vane structure; and
   a housing for supporting the screen structure; whereby rotation of the vane structure relative to the screen structure forces the first portion of the feed material through the screen structure.

10. A digester system as recited in claim 9, in which the vane structure defines at least one working edge in contact with the screen structure.

11. A digester system as recited in claim 9, in which:
   the screen structure is substantially frustoconical; and
   the vane structure defines at least one working edge; wherein
   the at least one working edge is angled such that substantially an entire portion of the at least one working edge is in contact with the screen structure.

12. A digester system as recited in claim 9, in which the thickener further comprises:
   a motor; and
   a transmission; wherein
   the transmission couples the motor to the vane structure such that
      operation of the motor causes rotation of the vane structure relative to the screen structure about a system axis, and
      the vane structure may move relative to the motor along the system axis as the vane structure wears.

13. A digester system as recited in claim 12, in which:
   the screen structure is substantially frustoconical; and
   the vane structure defines at least one working edge; wherein
   the at least one working edge is angled with respect to the system axis such that substantially an entire portion of the at least one working edge is in contact with the screen structure.

14. A waste processing system for waste slurry, comprising:
   a digester tank for containing feed material comprising liquids and solids, where
      the feed material comprises at least a portion of the waste slurry, and
      the digester tank generates a first digested material and biogas from the feed material;
   a thickener;
   a first conduit operatively connected between the thickener and the digester tank to allow a pre-thickened feed material to flow from the digester tank to the thickener;
   a second conduit operatively connected between the thickener and the digester tank to allow a thickened feed material to flow from the thickener to the digester tank; and
   a seal conduit operatively connected to the thickener to allow a second digested material to flow out of the thickener; wherein
   the seal conduit defines a corner portion arranged above the thickener and below a level of the feed material within the digester tank such that the corner portion and the thickener are flooded with feed material substantially to prevent the thickener from allowing entrained biogas in the pre-thickened feed material from exiting the thickener with the second digested material.

15. A waste processing system as recited in claim 14, in which the seal conduit is configured to maintain back pressure on the second digested material flowing out of the thickener.

16. A waste processing system as recited in claim 14, further comprising a vacuum break arranged in the corner portion of the seal conduit.

17. A waste processing system as recited in claim 16, in which the vacuum break terminates above the level of feed material within the digester tank.

18. A waste processing system as recited in claim 14, further comprising a separator for separating the waste slurry into a first slurry portion and a second slurry portion, where the feed material comprises the first slurry portion.

19. A waste processing system as recited in claim 14, further comprising:

a first separator for separating the waste slurry into a first slurry portion and a second slurry portion, where the feed material comprises the first slurry portion; and a second separator for separating the second slurry portion into a third slurry portion and a fourth slurry portion, where the feed material further comprises the third slurry portion.

20. A waste processing system as recited in claim 19, in which the fourth slurry portion is used to form at least a portion of the waste slurry.

21. A waste processing system as recited in claim 18, further comprising a batch tank, where the batch tank combines the first slurry portion with water to obtain the feed material.

22. A waste processing system as recited in claim 19, further comprising a batch tank, where the batch tank combines the first slurry portion, the third slurry portion, and water to obtain the feed material.

23. A waste processing system as recited in claim 14, further comprising:
a first separator for separating the waste slurry into a first slurry portion and a second slurry portion, where the feed material comprises the first slurry portion;
a second separator for separating the second slurry portion into a third slurry portion and a fourth slurry portion; and
a third separator for separating the third slurry portion into a fifth slurry portion and a sixth slurry portion, where the feed material further comprises the fifth slurry portion; and
a fourth separator for separating the sixth slurry portion into a seventh slurry portion and an eighth slurry portion, where the feed material further comprises the seventh slurry portion.

24. A waste processing system as recited in claim 23, in which the fourth slurry portion is used to form at least a portion of the waste slurry.

25. A waste processing system as recited in claim 23, further comprising a batch tank, where the batch tank combines the first slurry portion, the fifth slurry portion, the seventh slurry portion, and water to obtain the feed material.

26. A waste processing system as recited in claim 18, further comprising a separator for separating the first digested material into a liquid portion and a solids portion.

27. A waste processing system as recited in claim 26, further comprising a storage facility for storing the liquid portion of the first digested material.

28. A waste processing system as recited in claim 27, in which the storage facility further stores the second digested material and the eighth slurry portion.

29. A waste processing system as recited in claim 15, further comprising a thickener pump for causing at least a portion of the feed material to flow from the digester tank through the first conduit, through the thickener, and back into the digester tank through the second conduit.

30. A waste processing system as recited in claim 14, in which the thickener comprises a screen structure, where the second digested material flows through the screen structure and out of the thickener.

31. A waste processing system as recited in claim 30, in which the thickener further comprises:
a vane structure; and
a housing for supporting the screen structure; whereby rotation of the vane structure relative to the screen structure forces the first portion of the feed material through the screen structure.

32. A waste processing system as recited in claim 31, in which the vane structure defines at least one working edge in contact with the screen structure.

33. A waste processing system as recited in claim 31, in which:
the screen structure is substantially frustoconical; and
the vane structure defines at least one working edge; wherein
the at least one working edge is angled such that substantially an entire portion of the at least one working edge is in contact with the screen structure.

34. A waste processing system as recited in claim 31, in which the thickener further comprises:
a motor; and
a transmission; wherein
the transmission couples the motor to the vane structure such that
operation of the motor causes rotation of the vane structure relative to the screen structure about a system axis, and
the vane structure may move relative to the motor along the system axis as the vane structure wears.

35. A waste processing system as recited in claim 34, in which:
the screen structure is substantially frustoconical; and
the vane structure defines at least one working edge; wherein
the at least one working edge is angled with respect to the system axis such that substantially an entire portion of the at least one working edge is in contact with the screen structure.

36. A method of digesting feed material comprising liquids and solids, the method comprising the steps of:
arranging the feed material within a digester tank;
combining the feed material with microorganisms within the digester tank to generate a first digested material and biogas from the feed material;
allowing a pre-thickened feed material to flow from the digester tank to a thickener;
allowing a thickened feed material to flow from the thickener to the digester tank;
removing a second digested material from the pre-thickened feed material using the thickener such that the thickened feed material alters a solid content of the feed material in the digester tank; and
arranging a seal conduit such that the second digested material flows out of the thickener through the seal conduit and such that at least a corner portion of the seal conduit is above the thickener and below a level of the feed material within the digester tank such that
the corner portion and the thickener are flooded with feed material, and
back pressure is maintained on the second digested material within the thickener substantially to prevent biogas from being entrained within the second digested feed material leaving the thickener.

37. A method as recited in claim 36, in which the step of removing the second digested material comprises the step of maintaining the solid content of the feed material in the digester tank within a predetermined range.

38. A method as recited in claim 36, further comprising the step of pumping at least a portion of the feed material from the digester tank, through the thickener, and back into the digester tank.

39. A method as recited in claim 36, in which the step of removing the second digested material to alter the solid content of the feed material using the thickener comprises the step of causing the second digested material to flow through a screen.

* * * * *